United States Patent [19]
Benson

[11] Patent Number: 5,423,828
[45] Date of Patent: Jun. 13, 1995

[54] METHOD AND APPARATUS FOR SIMPLIFYING PROSTHETIC JOINT REPLACEMENTS

[75] Inventor: Gail M. Benson, Sioux Falls, S. Dak.

[73] Assignee: Bentwood Place, Inc., Sioux Falls, S. Dak.

[21] Appl. No.: 83,669

[22] Filed: Jun. 28, 1993

Related U.S. Application Data

[63] Continuation-in-part of Ser. No. 882,938, May 14, 1992, Pat. No. 5,318,571.

[51] Int. Cl.⁶ .............................................. A61B 17/56
[52] U.S. Cl. ...................................... 606/102; 606/53
[58] Field of Search ................. 33/512, 511, 732, 751; 606/53–59, 86, 87, 89, 91, 96, 102, 88

[56] References Cited

U.S. PATENT DOCUMENTS

| | | | |
|---|---|---|---|
| 3,394,459 | 7/1968 | Grant | 33/512 X |
| 3,643,651 | 2/1972 | Cuadros | 33/512 X |
| 4,279,260 | 7/1981 | Stump | 33/512 X |
| 4,843,720 | 7/1989 | Kim | 33/512 X |
| 4,846,194 | 7/1989 | Sabia | 33/512 X |
| 5,122,145 | 6/1992 | Fishbane | 606/102 |
| 5,148,606 | 9/1992 | Mason et al. | 33/512 |
| 5,156,162 | 10/1992 | Gerhardt | 33/512 X |
| 5,318,571 | 6/1994 | Benson | 606/102 |

FOREIGN PATENT DOCUMENTS 87002883  5/1987  WIPO ................ 606/102

Primary Examiner—Robert A. Hafer
Assistant Examiner—Brian E. Hanlon
Attorney, Agent, or Firm—Fredrikson & Bryon

[57] ABSTRACT

A method and apparatus for providing accurate measurement, in the course of an arthoplasty procedure, of the length dimension of a bone joint movable between an extended and flexed position.

6 Claims, 4 Drawing Sheets

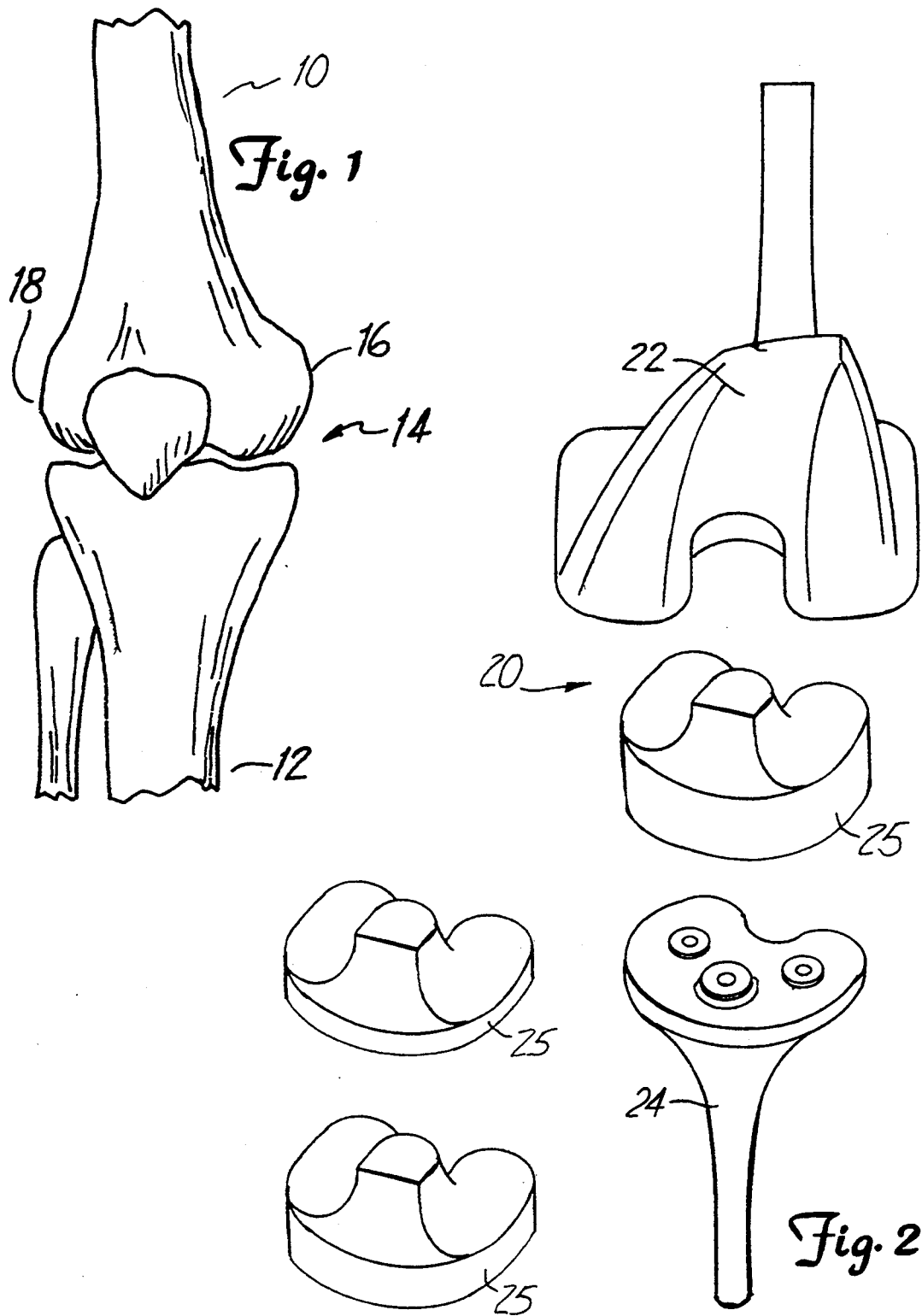

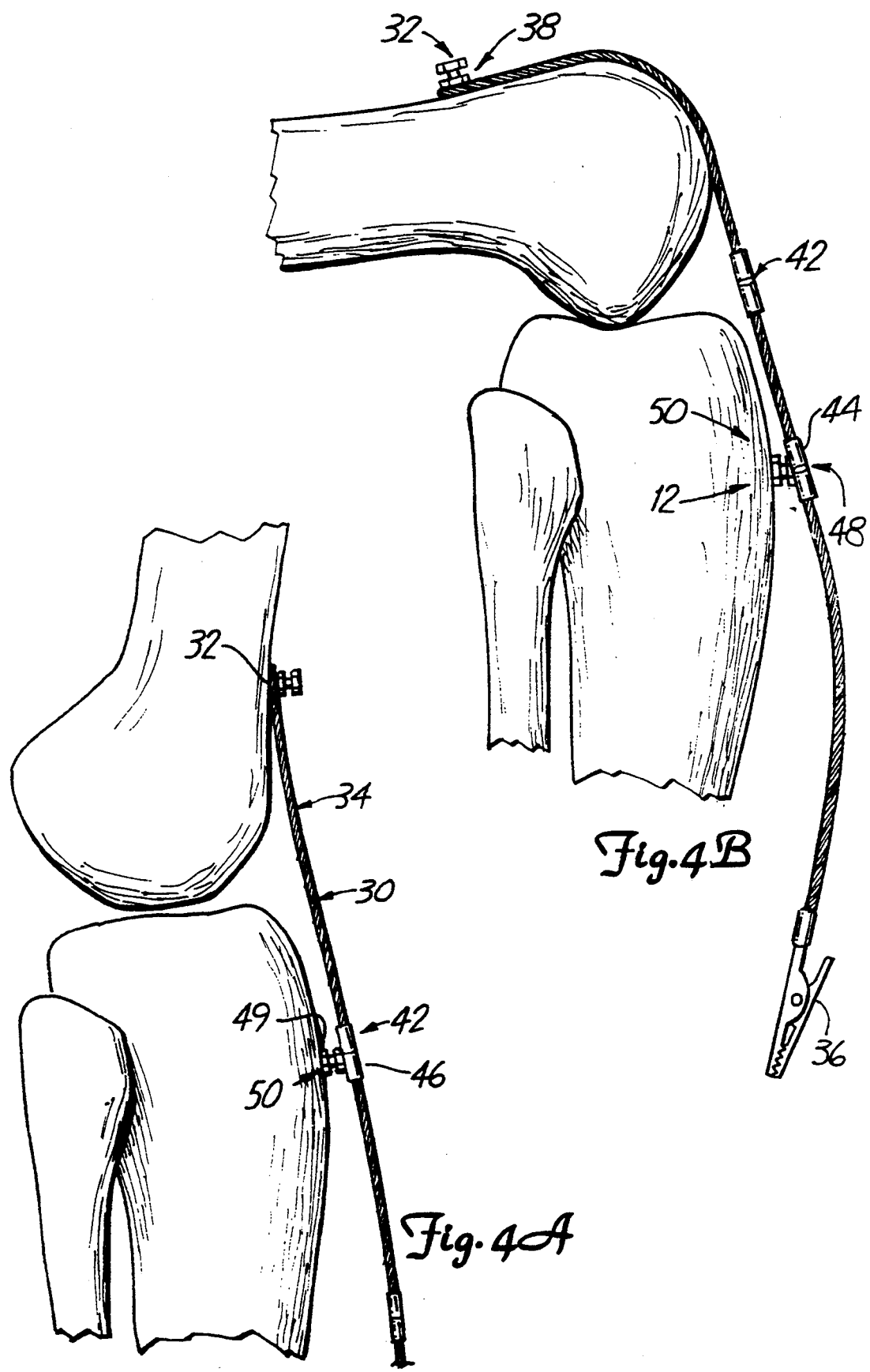

METHOD AND APPARATUS FOR SIMPLIFYING PROSTHETIC JOINT REPLACEMENTS

CROSS-REFERENCE TO RELATED APPLICATION

The present application is a continuation-in-part of U.S. patent application Ser. No. 07/882,938, filed May 14, 1992, U.S. Pat. No. 5,318,571, issued Jun. 7, 1994 and entitled METHOD AND APPARATUS FOR SIMPLIFYING TOTAL HIP ARTHROPLASTY.

FIELD OF THE INVENTION

The present invention relates to a method and apparatus for facilitating prosthetic joint replacement surgery for assuring that the resulting joint length in the range of motion between full extension and flexure is correct.

BACKGROUND OF THE INVENTION

The installation of replacement joint prostheses involves surgically exposing and dislocating the joint, and cutting away or resecting one or both of the portions of the bones making up the joint. The most common prosthetic joint surgical procedures are total hip, knee and finger joint procedures. Knee and finger joint arthroplasty procedures are undertaken to correct for degeneration in the mating joint bones and cartilage caused by injury or disease processes. Healthy knee and finger joints enjoy a range of motion between a fully extended and a fully flexed position which is desirable to reproduce with the implanted replacement prosthesis. Moreover, it is desired to reattach and reposition tendons and the patella (or artificial patellar component) in the proper anatomic positions to provide strength and support of the replacement joint and to inhibit dislocations and prevent implant failures.

With respect to knee arthroplasty, typically both components of the knee joint need to be replaced. Knee arthroplasty requires that the ends of the fibial bone and femoral bone (condyles) of the patient be resected, that is, cut and shaped in order to receive the respective tibial and femoral components of the prosthesis in proper alignment. In the placement of the tibial and femoral components, it is also often necessary to bore the respective bones to permit them to receive implant stems extending from each component.

The resection of the femoral and tibial bones typically results in the removal of cartilage and bone. The subsequent implantation of a standard size prosthesis could result in an overall shortening or lengthening of the joint.

One way surgeons avoid this problem is by implanting thicker knee components to compensate for the lost bone. For example, some femoral component designs are available in a variety of thicknesses, in order to obtain for various final sizes. For example, Howmedica, Inc. sells a "P.C.A." revision total knee system which has small, medium and large femoral components. The P.C.A. revision total knee system includes a series of tibial base inserts that fit upon the plate of the tibial component that are provided in various thicknesses and sizes. The surgeon has the choice of selecting from these available femoral and tibial components in order to approximate the over all dimensions of the patient's original knee joint. Frequently, surgeons choose the thickest tibial insert that will fit between the tibial plate and femoral component after the latter components are surgically attached so that the tendons extending therebetween are tightened up and little play is found in the joint as the knee is flexed.

The use of such a thick femoral component or tibial insert or an over-sized component to compensate for bone loss can, however, result in poor ligament balance, improper positioning of the joint line, and shifting of the patella position with a change of arc of motion (leading to dislocation). This, in turn, can cause poor tracking of the patella on the femoral component in the range of motion between full extension and the extent of flexure permitted by the design of the prosthesis. If the patella is improperly positioned, it may shift laterally with respect to the femoral component and dislocate off the front of the knee to a lateral position, causing the patient considerable distress due to pain and instability. This patellar instability will frequently occur if the joint is lengthened, whether or not the patellar surface is replaced. The patellar misalignment occurs primarily due to the relative lengthening of the joint, which increases the are of motion over the knee joint.

In addition, using the thicker or oversized components may also lengthen the patient's leg, causing an imbalance with the other leg that is obviously undesirable. Relative lengthening of the joint also results in loss of full extension and/or flexion.

In the presence of severe deterioration of the tibia, it is also known to fill in gaps in the resected tibia inferior to the plate of the tibial component so that the plate may be raised and a thinner tibial insert employed. See, for example, the article by Peter J. Brooks, M.D., et al, entitled "Tibial Component Fixation in Deficient Tibial Bone Stock," *Clinical Orthopedics and Related Research*, pp. 302–308, Vol. 184, April 1984. Similarly, femoral shims adapted to be positioned in the superior recess of the femoral component are disclosed in U.S. Pat. No. 4,731,086. Thus, the surgeon has available a number of techniques and components for approximating the original dimensions of the knee joint or for dimensionally correcting imbalanced dimensions in the arthroplasty procedure.

At present, however, surgeons typically rely on gross artatomic dimensional measurements of leg length and visual approximations of the knee joint. They further rely on trial and error insertions of tibial inserts of differing thicknesses in making the final determination of the components to be permanently implanted. See, for instance, "Asymmetrical Buildup and Prosthesis Sizing", pages 67–73, in *The Technique of Total Knee Arthroplasty*, K. A. Krackow, 1990, C. V. Mosby Co., which describes the pitfalls associated with the use of x-ray films as a preoperative means to determine approximate sizing requirements.

Thus, an object of this invention is to provide a simple, reproducible technique and apparatus for use in such arthroplasty procedures of a bone joint movable between an extended and a flexed position for simplifying the selection of these components, to regain accurate joint height and pateliar excursion length, and achieving a higher degree of consistency and predictability in the post-surgical operation of the joint prosthesis.

SUMMARY OF THE INVENTION

In accordance with the present invention, a method and apparatus is provided for making an accurate measurement of the length dimension of the joint prior to resection of the joint bones in both the extended and flexed joint positions and using those dimensions in the selection of and trial fitting of joint components so as to reproduce the characteristics of the natural joint prior to trauma or degeneration.

When used, for instance, in the implantation of a knee joint prosthesis, the method of using the apparatus of the present invention provides a true length measurement of the knee joint taken in extension and an arc of motion length over the proper patellar position in flexion. These measurements are used in selecting and fitting knee joint replacement prosthetic components to avoid the subsequent pateliar dislocation described above.

BRIEF DESCRIPTION OF THE DRAWING

These and other advantages and features of the present invention will become apparent from the following detailed description of the preferred embodiments thereof in conjunction with the drawings in which:

FIG. 1 is an anterior view of the flexed human right knee joint;

FIG. 2 is an illustration of a implantable knee joint prosthesis for total knee arthroplasty of a type employing separate femoral and tibial components;

FIGS. 4(a) and 4(b) are an illustration of the use of the calibration apparatus of FIG. 3 in initially measuring the distance between two points on the femoral and tibial bones in both the extended (FIG. 4a) and flexed (FIG. 4b) positions;

DESCRIPTION OF THE PREFERRED EMBODIMENTS

Figure 3:
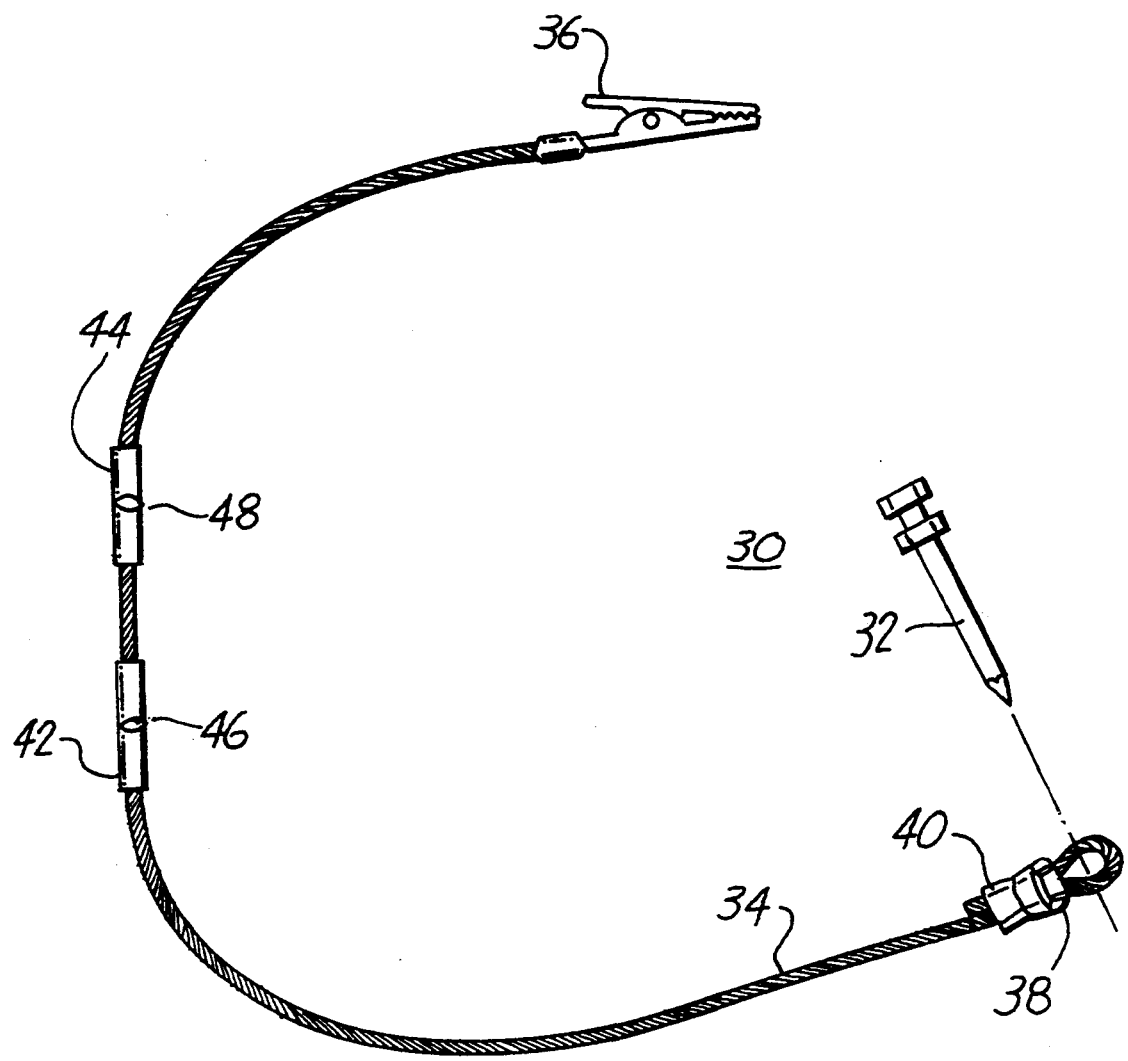
FIG. 3 is an illustration of a preferred embodiment of the calibration apparatus employed in the practice of the method of the present invention.

The present invention provides a measuring apparatus and method for use in bone joint replacement surgery for insuring that the replacement prosthesis is properly sized so that the resulting joint movement between fully extended and flexed positions mimics the original range of movement enjoyed by the patient prior to degeneration of the joint. A flexible measuring cable is securely attached at one end thereof to exposed bone on one side of the joint to be replaced and distal to any bone to be resected. The length of flexible cable is extended across the joint to be replaced and preferably in alignment with the plane of movement of the joint. A marking is made in the other bone of the joint along the extended length of the cable at a position distal to the area of resection of that bone.

The cable is also provided with first and second slidable markers which may be crimped into firm attachment with the cable by a suitable crimping tool. A first measurement is made with the bone joint in its extended position and a first marker is aligned with the reference point on the second bone and crimped to the cable. Then the joint is positioned in a predetermined angle of flexure, and the second slidable marker is aligned with the reference point on the second bone and crimped to the cable. Thereafter, in the surgical procedure for resection of the joint bones and attachment of the artificial joint prosthesis components, the flexible cable is pivoted out of the surgical field.

During the fitting of the trial and permanent components of the artificial joint prosthesis, the measuring cable may be positioned so that the first and second markers are aligned with the reference point on the second bone in the extended and flexed positions, respectively. In this fashion, joint components of suitable dimensions, including thickness, may be selected to reproduce the patient's original joint dimensions or to correct the joint dimensions to overcome degeneration of the patient's joint. The method and apparatus, which may be provided in kit form, has particular application in finger joint prosthetic surgery and in knee joint prosthetic surgery to ensure that the patella is accurately repositioned following surgery.

Thus, in accordance with the present invention, an apparatus is provided for making an accurate dimensional measurement of the length of the bone joint between first and second reference points which comprises a length of flexible cable having first and second ends, first means for pivotally attaching the first end of the length of the flexible cable to a first position on the bone of the patient such that the length of flexible cable may be extended in a direction across the bone joint to be replaced and over the second reference point on the second bone of the joint. The cable may be repositioned to other positions out of the surgical field when not used for measurement.

The apparatus further comprises first distance indicating means along the cable for permanent attachment to the cable for measuring a distance from the first reference point to the second reference point while the first and second bones are in the extended position afforded by the bone joint. The apparatus further comprises second distance indicating means along the cable for permanent attachment to the cable for measuring a second distance from the first reference point to the second reference point when the first and second bones are positioned at a predetermined angle of flexure afforded by the joint. The first and second distances marked on the flexible cable may be employed in sizing prosthetic joint components during trial fittings thereof in the extended and flexed positions.

The invention relates in one aspect to a method for facilitating prosthetic joint replacement surgery and for making an accurate dimensional measurement of the length of the bone joint, the method comprising the steps of:

(a) surgically exposing the portions of the first and second bones making up the joint;

(b) marking or forming a first reference point on the first bone and a second reference point on the second bone;

(c) providing an apparatus comprising a length of flexible cable having first and second ends and first means for pivotally attaching the first end of the length of the flexible cable to the first reference point such that the length of flexible cable may be extended in a direction across the bone joint to be replaced and over the second reference point on the second bone of the joint, the apparatus further comprising first distance indicating means for permanent attachment to the cable for measuring a distance along the cable from the first reference point to the second reference point while the first and second bones are in the extended position afforded by the bone joint, and second distance indicating means for permanent attachment to the cable for measuring a second distance along the cable from the first reference point to the second reference point when the first and second bones are positioned at a predetermined angle of flexure afforded by the joint;

(d) pivotally attaching the first end of the cable to the first reference point using the first attachment means;

(e) permanently attaching the first distance indicating means to the cable in order to mark the position of the first reference point along the length of the cable while the first and second bones are in the extended position afforded by the bone joint;

(f) permanently attaching the second distance indicating means to the cable in order to mark the position of the second reference point along the length of the cable while the first and second bones are positioned at a predetermined angle of flexure afforded by the joint, (g) performing the surgical task of implanting a joint prosthesis;

(h) using the first and second indicated distances to select and fit joint replacement prosthetic components.

Optionally, the method can involve the further step of adjusting or replacing such components if needed to provide the desired distance and fit between said attachments, the distance correcting any noted disparity in the extended and flexed positions of the joint. The first and second distances marked on the flexible cable may be similarly employed in sizing prosthetic joint components during trial fittings thereof in the extended and flexed positions.

Turning now to the Drawing and first to FIG. 1, it illustrates an anterior view of the flexed human knee joint. The femur 10, or thigh bone, articulates at its distal end with the tibia 12 at the knee joint 14. The shaft of the femur bows medially so that it approaches the femur of the opposite thigh. As a result of this convergence, the knee joints are brought together to the body's line of gravity or weight supporting axis.

The distal end of the femur is expanded and includes the medial condyle 16 and the lateral condyle 18. These articulate with the tibia and (with attendant ligaments, etc.) to form the knee joint 14.

Through disease processes or injury, the knee joint may become less mobile, painful or totally unusable, requiting surgical intervention and a total knee arthroplasty employing a knee joint prosthesis of the type described in the above-referenced publications. A wide variety of prostheses are available from several manufacturers, the prostheses typically including a femoral component for surgical replacement of the natural condyles and femoral groove, and a tibial implant comprising a tibial surface and shaft of the type illustrated in FIG. 2.

Turning now to FIG. 2, it illustrates a typical knee prosthesis 20. The prosthesis 20 is usually made of biocompatible and inert materials and is available in a number of cross-section shapes and sizes having varying exterior contours. In practice, manufacturers of knee prostheses provide a selection of different sizes and shapes of femoral implants 22 and tibial implants 24. As shown, a tibial implant 24 frequently includes a tibial base having a stem for insertion into the tibial itself. In use, the tibial implant base 24 is typically used together with a tibial tray 25 that will contact the femoral component and is removably attached to the base at the time of surgery. Trays are typically provided as depicted in FIG. 2, that is, in varying sizes, particularly various thicknesses, thereby allowing the surgeon to choose the size best suited to the patient's needs. Thus, it is possible to customize the components as necessary in order to replicate the proper knee dimensions for the individual patient.

As described above, inaccurate sizing of a joint prosthesis such as a knee prosthesis can result in an overall shortening or lengthening of the joint and leg. I have found that the operative procedure may be simplified and the need to provide corrective action or reoperate substantially eliminated by providing a plurality of measurements between respective fixed points of the bone making up the joint in both the extended and flexed positions prior to resection of the bones themselves.

Figures 5A, 5B:
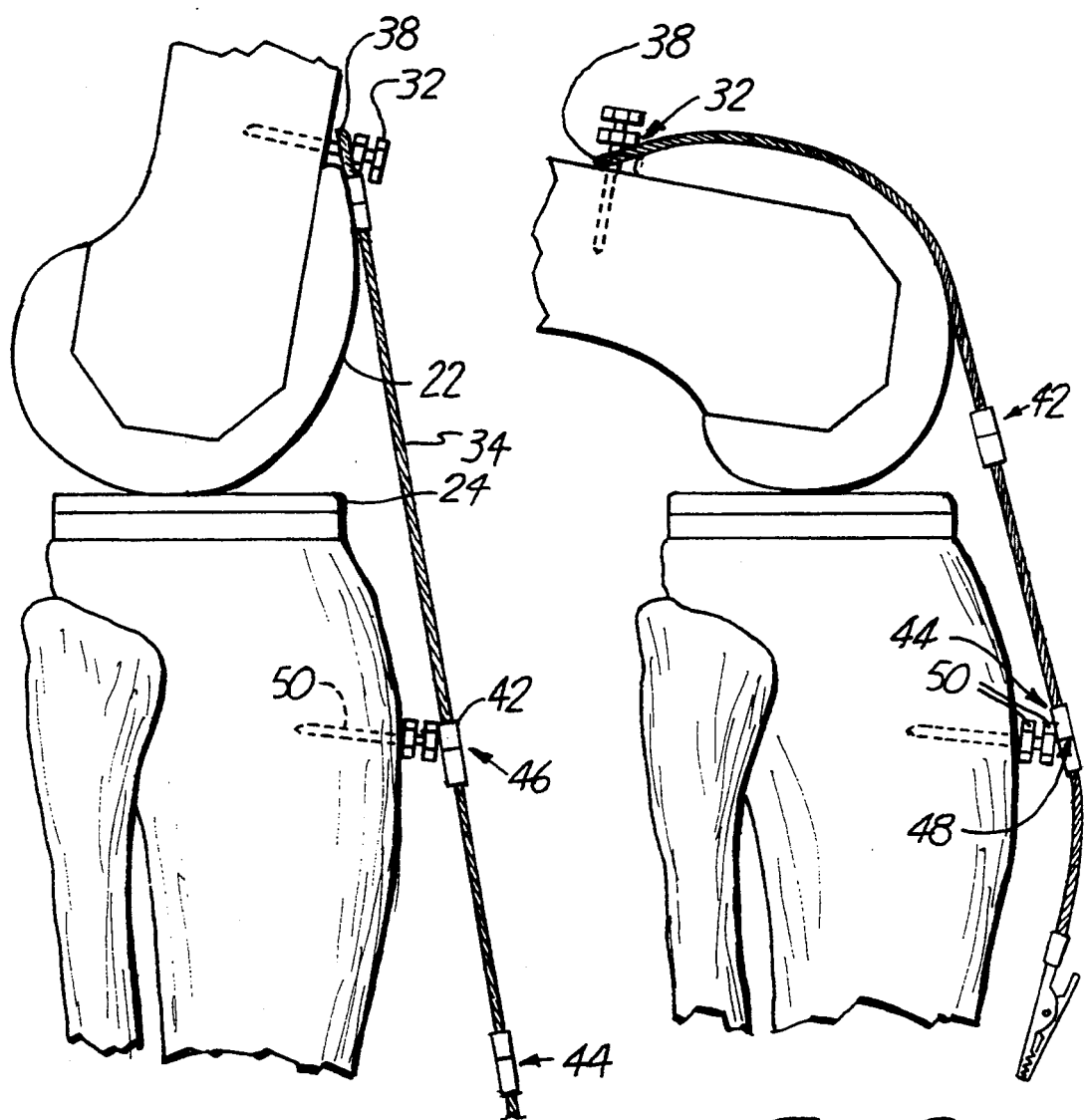
FIGS. 5(a) and 5(b) are an illustration of the use of the calibration apparatus of FIG. 3 in measuring the distance between two points on the femoral and tibial bones in the course of fitting trial prosthesis components with the knee in both the extended (FIG. 5a) and flexed (FIG. 5b) positions.

To this end, FIG. 3 illustrates a calibration apparatus 30 comprising length of cable 34 and a bone nail 32 that are used as illustrated in FIGS. 4 and 5 to select a properly sized joint prosthesis 20 during the procedure and avoid reoperation. The calibration apparatus depicted in FIG. 3 comprises a length of stranded wire cable 34 extending between an alligator clip 36 and a loop 38 formed by bending the cable 34 back against itself and crimping a crimp tube 40 around both to form a loop. The loop 38 is placed around the bone nail 32 as it is fixed in the region of the of the femur as shown in FIG. 4. The alligator clip 36 is provided so that the free end of the cable 34 may be attached to a surgical drape to hold the apparatus 30 out of the surgical field when it is not used in the manner depicted in FIGS. 4 and 5.

The calibration apparatus 30 depicted in FIGS. 3-5 also includes a first 42 and second 44 slidable tubes, having a calibration marks 46 and 48, respectively, on their outer surfaces. The calibration tubes may be slid back and forth on the length of stranded wire cable 34 so that the marks are aligned with the second reference point on the tibia 12, in both the extended and flexed positions, and crimped in place by a crimping tool.

Turning now to FIG. 4, it illustrates the placement of the calibration apparatus 30 to effect measurements of distance between reference points on both the femur 10 and the tibial bone 12 before the joint is dislocated and the bones resetted. It will be understood that for the sake of simplicity, the operating field, including the incision and the separation of the muscles and ligaments, are not illustrated in FIGS. 4 and 5. Assuming that those operative steps have been taken and the distal end of the femur 10 and tibia 12 are exposed, the surgical nail 32 is driven into the region of femur distal from the joint after the loop 38 in the cable 34 has been mechanically attached to the head of the nail 32. Thereafter, the cable 34 is extended in the direction of the leg in the extended position, bringing the cable over or alongside the tibia. Then, as shown in FIG. 4, the first slidable calibration tube 42 is moved along the length of cable 34 until one of its indicating mark 46 is aligned with a reference point 50 made on the tibia. The reference point 46 may in fact be a further surgical nail 49 driven into the tibia itself since it may be difficult to otherwise mark the bone.

After the indicating mark 46 and second reference point 50 are aligned, the tube 42 is crimped tightly against the stranded wire cable 34 so that it cannot be moved or dislodged. As seen in FIG. 4b, the process is repeated with the leg positioned in a predetermined angle of flexure in order to align mark 48 and attach the second slidable marker 44 with respect to the second reference point. The cable 34 can then be pivoted superiorly out of the operating field. The alligator clip 36 is attached to a surgical drape covering the patient's leg in order to keep the apparatus 30 out of the surgical field to allow the surgeon to dislocate the joint and proceed with the resection of the femur and tibia, the reaming of the tibial canal to accept the trial tibial components in the manner described in the above-incorporated publications, and the surgical placement of the prosthesis.

Turning now to FIG. 5, it illustrates the placement of an artificial knee prosthesis 20 by the insertion of a trial femoral component upon the resected femur 10. Once the femoral component 22 is surgically implanted and the tibial canal is reamed out, a trial tibial implant 24 is inserted as shown in FIG. 5 to test the fit and the articulation of the knee. As described above, the failure to select the proper size of either the femoral or tibial implants may cause the patient to suffer from an imbalance in the resulting leg length.

In accordance with the method of my invention, the calibration apparatus 30 is employed in the trial fitting stage to ensure that the selected prosthetic components result in the desired fit and leg length. As illustrated in FIG. 5, once trial femoral and tibial implants are in place, the stranded wire cable 34 can be extended in the direction of the tibia, with the leg in both the extended and the predetermined flexed positions, in order to align it with the second reference point thereon. If the measurements indicate that the actual position, at either extension or flexure, is superior or inferior to the noted calibration indicia 46 and 48, then either the trial implants are withdrawn and/or longer or shorter components are substituted and/or wedges or inserts are used in order to bring the implants to their final desired relationship. The process is repeated until the extended and flexed distances between reference points are aligned as closely as possible with both the first and second measurements.

After the properly sized components are installed, the surgical nail 32 and 49 (if used) as well as the cable 34 are removed and the incision is closed in the normal manner. By use of the inventive tool and procedure, the incidence of reoperation or other post-operative actions required to correct for post-operative problems due to incorrect sizing is virtually eliminated.

The invention has been described in detail with particular reference to the preferred embodiments thereof, but it will be understood that variations and modifications can be effected within the spirit and scope of the invention.

What is claimed is:

1. Apparatus for use in orthopedic and reconstructive surgery conducted on a patient, the apparatus being useful for making skeletal distance measurements between first and second reference points on first and second bones making up a joint, comprising:
   a length of flexible cable having first and second ends;
   first means for pivotally attaching said first end of said length of flexible cable to skeletal bone of said patient at said first reference point such that said length of flexible cable may be extended in a desired direction alongside said second reference point to effect a desired skeletal distance measurement therebetween and may be repositioned to other positions out of surgical field when not used for such measurement;
   first distance indicating means for permanent attachment to said cable and moveable along the length of said cable for measuring a distance from said first reference point to said second reference point while said first and second bones are in the extended position afforded by said bone joint;
   second distance indicating means for permanent attachment to said cable and moveable along said length of said cable for measuring a second distance from said first reference point to said second reference point when said first and second bones are positioned at a predetermined angle of flexure afforded by the joint
   whereby said first and second distance indicating means can be attached to said cable at points along the length of said cable related to said second reference point and said length of flexible cable may be moved to said other positions during reconstructive surgery conducted on said patient.

2. The apparatus of claim 1 wherein said first and second distance indicating means each comprise a tubular, slidable member fitting over and around said length of flexible cable and slidable between the first and second ends thereof, the tubular members each having at least one calibration indicia on its surface and being fabricated of a material capable of being crimped against the flexible cable in order to mark the measured distance therealong.

3. The apparatus of claim 2 further comprising:
   attaching clip means coupled to said second end of said length of flexible cable for allowing said second end of said flexible cable to be attached out of and away from the operating field.

4. The apparatus of claim 1 further comprising:
   attaching clip means coupled to said second end of said length of flexible cable for allowing said second end of said flexible cable to be attached out of and away from the operating field.

5. Apparatus for aiding reconstructive knee surgery involving the replacement of a dysfunctional knee joint with an artificial orthopedic prosthesis comprising:
   a length of flexible cable having first and second ends;
   means for affixing said first end of said length of flexible cable to a patient's femoral bone at a first reference point such that said length of flexible cable may be extended in a straight line alongside the knee joint and generally over the tibial bone;
   means for marking a second reference point on the patient's tibia;
   first distance indicating means for permanent attachment to said cable and moveable along the length of said cable for measuring a distance from said first reference point to said second reference point while said first and second bones are in the extended position afforded by said bone joint;
   second distance indicating means for permanent attachment to said cable and moveable along said length of said cable for measuring a second distance from said first reference point to said second reference point when said first and second bones are positioned at a predetermined angle of flexure afforded by the joint;
   attaching clip means coupled to said second end of said length of flexible cable for allowing said second end of said flexible cable to be attached out of and away from the operating field.

6. The apparatus of claim 5 wherein said first and second indicating means each comprise a tubular, slidable member fitting over and around said length of flexible cable and slidable between the first and second ends thereof, the tubular members each having at least one calibration indicia on its surface and being fabricated of a material capable of being crimped against the flexible cable in order to mark the distance between said first and second reference points.

* * * * *